United States Patent [19]
Kline et al.

[11] Patent Number: 5,883,227
[45] Date of Patent: Mar. 16, 1999

[54] MULTIPLE SCLEROSIS ASSOCIATED POLYPEPTIDE

[75] Inventors: Ellis L. Kline, Pendleton, S.C.; Daniel H. Zimmerman, Bethesda, Md.

[73] Assignees: Molecullar Rx, Inc., Pendleton, S.C.; Cell Med, Inc., Bethesda, Md.

[21] Appl. No.: 738,259

[22] Filed: Oct. 28, 1996

Related U.S. Application Data

[63] Continuation of Ser. No. 487,066, Jun. 7, 1995, Pat. No. 5,645,997, which is a continuation of Ser. No. 166,171, Dec. 16, 1993, abandoned, which is a continuation-in-part of Ser. No. 992,641, Dec. 18, 1992, abandoned.

[51] Int. Cl.⁶ ........................ C07K 14/435; C07K 16/00
[52] U.S. Cl. ........................ 530/350; 530/353; 530/361; 530/380; 530/388.1; 530/388.15; 530/388.73; 530/388.75; 530/388.85; 530/403; 530/412; 530/829; 530/837; 530/838; 530/839; 424/184.1; 435/7.1; 435/7.24
[58] Field of Search ........................ 530/350, 353, 530/361, 380, 388.1, 388.15, 388.73, 388.75, 388.85, 403, 412, 829, 837, 838, 839; 424/184.1; 435/7.1, 7.24; 204/182.8

[56] References Cited

U.S. PATENT DOCUMENTS

| | | |
|---|---|---|
| 3,864,481 | 2/1975 | Hashim . |
| 3,929,982 | 12/1975 | Coggins . |
| 3,932,601 | 1/1976 | Coggins . |
| 4,113,858 | 9/1978 | Hashim . |
| 4,294,818 | 10/1981 | McMichael et al. . |
| 4,376,110 | 3/1983 | David et al. . |
| 4,486,530 | 12/1984 | David et al. . |
| 4,918,163 | 4/1990 | Young et al. . |

OTHER PUBLICATIONS

Norton 1984 Ann. N.Y. Acad. Sci vol. 436, 5–10.

Current Protocols in Immunology editing by Coligan John, (1991, vol. 1, pp. 2.5.1, 2.5.2).

*Primary Examiner*—Paula K. Hutzell
*Assistant Examiner*—Khalid Masood
*Attorney, Agent, or Firm*—Jones & Askew, LLP

[57] ABSTRACT

The present invention relates to the diagnosis of multiple sclerosis. More specifically, this invention relates to an assay for detecting antigen(s) associated with multiple sclerosis. The present invention also relates to the generation of hybridomas which produce monoclonal antibodies which are specific for the multiple sclerosis-associated antigens. The present invention's use is in diagnosing multiple sclerosis and in routine follow-up monitoring of multiple sclerosis patients as to disease progression or response to therapy.

9 Claims, 5 Drawing Sheets

MULTIPLE SCLEROSIS ASSOCIATED POLYPEPTIDE

CROSS-REFERENCE TO RELATED APPLICATIONS

This application is a continuation of U.S. patent application Ser. No. 08/487,066, filed Jun. 7, 1995, (U.S. Pat. No. 5,645,997) which is a continuation of U.S. patent application Ser. No. 08/166,171, filed Dec. 16, 1993, (ABN) which is a continuation-in-part of U.S. patent application Ser. No. 07/992,641, filed Dec. 18, 1992, (ABN).

TECHNICAL FIELD

The present invention relates to the detection of demyelinating diseases such as multiple sclerosis. More specifically, this invention relates to an assay for detecting antigen(s) associated with multiple sclerosis and related diseases. The present invention also relates to the generation of hybridomas which produce monoclonal antibodies which are specific for the multiple sclerosis-associated antigens. The present invention's use is in diagnosing multiple sclerosis and in routine follow-up monitoring of multiple sclerosis patients as to disease progression or response to therapy.

BACKGROUND OF THE INVENTION

Multiple sclerosis is a slowly progressive disease of the central nervous system ("CNS"), characterized pathologically by disseminated patches of demyelinization in the brain and spinal cord, and clinically by multiple symptoms and signs with remissions and exacerbations. Demyelinization is the removal of the myelin, a protective, lipid substance that surrounds the axon of nerve fibers. Multiple sclerosis related diseases are those conditions which exhibit demyelinization of nerves.

Onset of multiple sclerosis is usually insidious. Commonly, minor visual disturbances, a fleeting ocular palsy, transient weakness, slight stiffness or unusual fatigability of a limb, minor interference with walking, difficulties with bladder control, occasional dizziness, or mild emotional disturbances—all evidence of scattered involvement of the CNS—occur months or years before the disease is recognized.

Among the varied symptoms of multiple sclerosis are the following: paresthesias involving one or more extremities or one side of the face, weakness or heaviness of the limbs; visual disturbances such as partial blindness in one eye, double vision, dimness of vision, or visual scotomas; bladder dysfunction; and mood disorders. (Paresthesias is an abnormal sensation, such as burning, prickling, and formication.)

Spontaneous remissions make any treatment difficult to evaluate. Though the average duration of life is 10 to 20 years following onset, many patients live longer. Some patients have frequent attacks and are rapidly incapacitated, while others have remissions that last as long as 25 years.

Diagnosis of the disease state is difficult owing to the overlap of the above-noted symptoms of multiple sclerosis and similar symptoms of other CNS diseases. Diagnosis of multiple sclerosis is most frequently premised upon a history of remissions and exacerbations of the various symptoms over a period of years in combination with systematic elimination of other possible diseases which display similar symptoms. Extensive testing, at substantial cost and often physical discomfort to the patient, is performed to eliminate the following diseases as the source of the symptoms: intracranial lesions, cerebrovascular accidents, acoustic neuroma, cerebellar tumors, gliomas of the brain stem, spinal cord tumors, syphilis, pernicious anemia, arthritis of the cervical spine, ruptured intervertebral disk, platybasia, and hereditary ataxia.

Substantial efforts have been directed toward development of diagnostic methods and materials useful in the early diagnosis of multiple sclerosis. Positive results in colloidal gold tests on cerebrospinal fluids are considered supportive, but not dispositive of a positive diagnosis. Also, the same is true of testing for elevated gamma globulin in cerebrospinal fluids—the test tends to verify diagnosis in advanced stages but is not helpful in diagnosis of early stages. Similarly, active demyelinization associated with the disease frequently is signified by elevation of analytical results in basic protein assay testing of spinal fluid, but test levels drop rapidly once acute exacerbation is over. Non-dispositive correlations have been made between the presence of the disease state and elevated levels of measles antibodies in serum and cerebrospinal fluids. Finally, certain researchers have proposed that electron microscopic examination of lymphocytes for certain distinct morphological changes may provide a fruitful basis for diagnosis of multiple sclerosis.

U.S. Pat. No. 4,294,818, describes a potential immunological marker for multiple sclerosis. This marker was not purified or characterized. In addition, there was no indication in the prior art that all or most animals responded with production of the proper isotype and amount of antibodies, and no demonstration was made that all or most animals from different species would respond in a consistent manner. Some or all of these requirements are necessary for commercial applications as, for example, with the use of antisera in a diagnostic test.

There remains a substantial need for diagnostic methods and materials for rapidly, simply, and accurately determining the presence of multiple sclerosis. Such methods should be highly specific for multiple sclerosis and closely related diseases to avoid the generation of false positive results due to other central nervous system diseases, other immune disorders or ingested drugs. Further, such methods should be capable of diagnosing multiple sclerosis in its early stages, should not involve painful or hazardous withdrawals of patient tissue samples, and should preferably involve standardized laboratory techniques which do not require expensive or complex apparatus.

SUMMARY OF THE INVENTION

The present invention relates to a method of detecting multiple sclerosis in a patient. The present invention also relates to either polyclonal or monoclonal antibodies specific for antigens related to the presence of multiple sclerosis. Such antibodies are used in immunoassays for the detection of the multiple sclerosis-associated antigens, therefore enabling a diagnosis of multiple sclerosis.

The present invention also relates to the characterization of a monoclonal antibody producing cell line designated HB11152 in the American Type Culture Collection ("ATCC") which shows specificity for an epitope on multiple sclerosis-associated antigens in patients suffering from multiple sclerosis. The present invention also relates to the characterization of a monoclonal antibody producing cell line designated HB11153 by the ATCC which shows specificity for an epitope on multiple sclerosis-associated antigens in multiple sclerosis patients.

This invention also includes any antibody preparation comprising a diagnostically effective amount of antibody, or binding fragment thereof, which competitively inhibits the binding of the monoclonal antibody produced by the hybridoma cell line ATCC No. HB11152 or ATCC HB11153 to the multiple sclerosis-associated antigens as measured by an enzyme immunoassay or other competitive inhibition immunoassay. This includes any antibody, or binding fragment thereof, that inhibits the binding of HB11152 or HB11153 antibodies with their respective epitopes on the multiple sclerosis-associated antigens. Epitopes are the structural component of an antigen molecule responsible for its specific interaction with antibody molecules.

The present invention also provides a method and composition for alleviating the symptoms of disease states associated with demyelination as is observed in multiple sclerosis. The present invention comprises administration to the human or animal with the multiple sclerosis an effective dose of the multiple sclerosis-associated antigens or its associated nucleotide sequences. The effective dose is at a level which does not cause side effects such as an anaphylactic response.

Specific antigenic markers for multiple sclerosis, antibodies specific for the markers, and an associated test for the diagnosis of multiple sclerosis have been unknown until this invention.

Accordingly, it is an object of this invention to provide a sensitive immunoassay for the detection of multiple sclerosis in humans.

It is another object of this invention to provide an immunoassay that is highly specific for the detection of multiple sclerosis and does not yield false positive results in patients with other central nervous system diseases.

It is another object of this invention to provide a sensitive immunoassay for the early detection of multiple sclerosis in humans.

It is another object of the present invention to provide a sensitive immunoassay for routine follow-up monitoring of multiple sclerosis patients as to disease progression or response to therapy.

It is yet another object of the present invention to provide a cost-effective method of detecting multiple sclerosis; as opposed to the current method which consists of a series of tests to eliminate all other similar, related nervous disorders.

It is another object of the present invention to provide a rapid method of detection of multiple sclerosis by immunoassay.

It is another object of the present invention to provide a single, definitive test for multiple sclerosis.

It is another object of the present invention to allow the treatment of multiple sclerosis patients to begin as rapidly as possibly as only one test is involved in the diagnosis of multiple sclerosis.

It is another object of the present invention to provided a method and composition for alleviating the symptoms of disease states associated with demyelinating diseases such as multiple sclerosis It is another object of the present invention to provide a purified protein which is associated with the presence of multiple sclerosis or other related demyelinating disease in a human or animal.

These and other objects, features and advantages of the present invention will become apparent after a review of the following detailed description of the disclosed embodiment and the appended claims.

DETAILED DESCRIPTION

Figure 1:
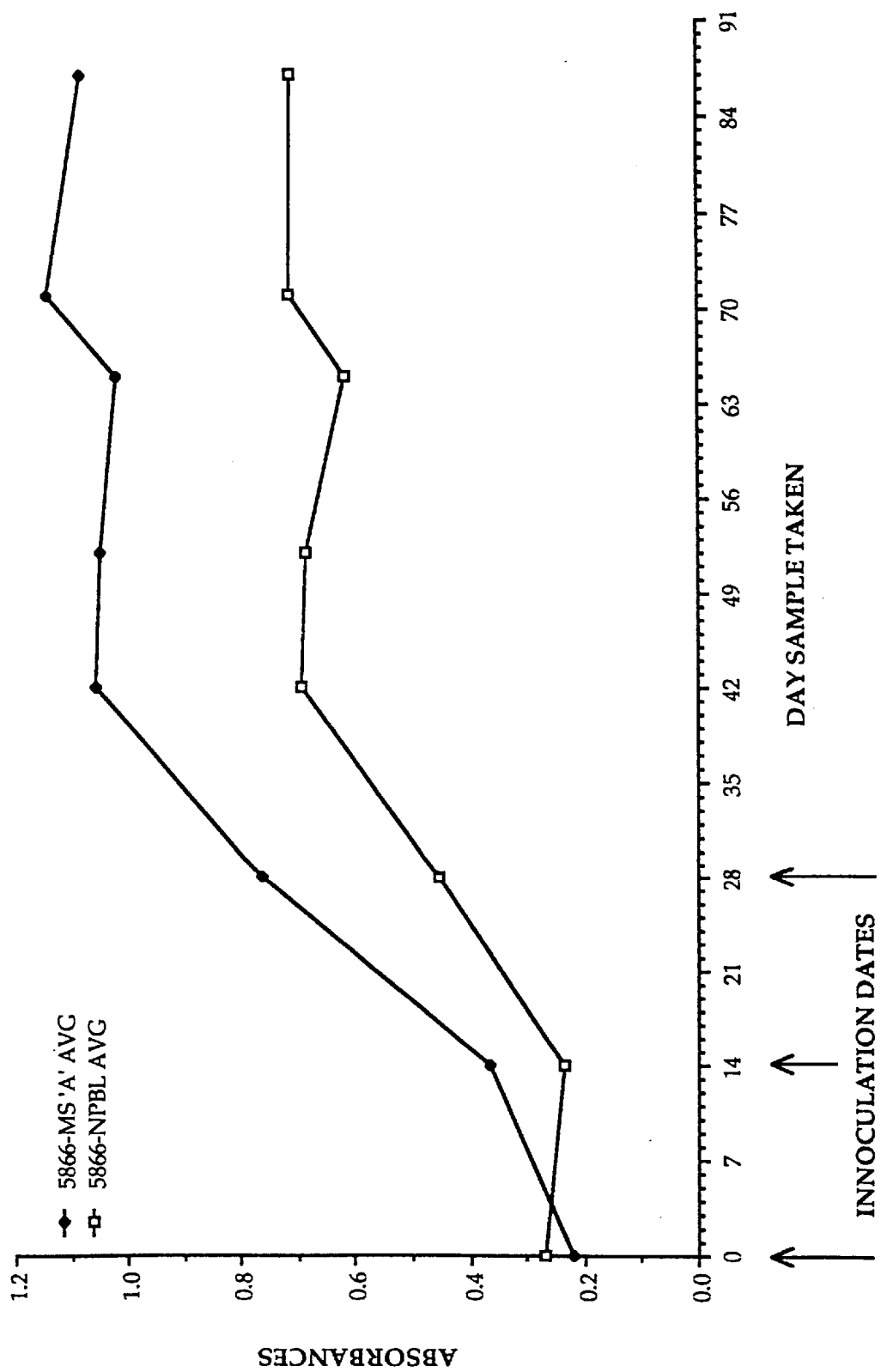
FIG. 1 illustrates the results of the immunoassay on the antisera obtained from several rabbits immunized with the multiple sclerosis PBL extract and tested with multiple sclerosis antigen(s) or an extract from normal cells.

The present invention relates to a method of detecting multiple sclerosis in a patient. The present invention also relates to polyclonal or monoclonal antibodies specific for antigens related to the presence of multiple sclerosis. Such antibodies can be used in immunoassays for the detection of the multiple sclerosis-associated antigens, therefore enabling a diagnosis of multiple sclerosis.

The present invention also relates to a monoclonal antibody produced by the cell line designated HB11152 by the ATCC which has specificity for an epitope on multiple sclerosis-associated antigens which occurs in patients suffering from multiple sclerosis. The present invention also relates to the characterization of a monoclonal antibody produced by the cell line designated HB11153 by the ATCC which shows specificity for an epitope on multiple sclerosis-associated antigens in multiple sclerosis patients.

The present invention also includes any antibody preparation comprising a diagnostically effective amount of antibody, or binding fragment thereof, which competitively inhibits the binding of the monoclonal antibody produced by the hybridoma cell line ATCC No. HB11152 or HB11153 to multiple sclerosis-associated antigens as measured by an enzyme immunoassay or other competitive inhibition immunoassay. This includes any antibody, or binding fragment thereof, that inhibits the binding of HB11152 or HB11153 antibodies with their respective epitopes on the multiple sclerosis-associated antigens. Epitopes are the structural component of an antigen molecule responsible for its specific interaction with antibody molecules.

According to the present invention, the antibodies that are produced by the cell lines HB11152 and/or HB11153 or antibodies that competitively inhibit binding by the antibodies produced by the HB11152 or the HB11153 cell lines can be used in any assay which utilizes antibodies to detect the antigens. This includes enzyme linked immunoassays, radioimmunoassays, fluorescent immunoassays, bioluminescent and chemiluminescent immunoassays, competitive immunoassays, dot blot technology, and Western blot assays.

The present invention also includes a purified protein or proteins or their associated RNA or DNA nucleotide sequences which has been shown to be associated with the presence of multiple sclerosis and related demyelinating diseases. The analysis of DNA sequences is well known to those of ordinary skill in the art and include Southern blotting and Northern hybridization procedures as described in Current Protocols in Immunology, Vol. 2, edited by John E. Coligan, et al. pgs 10.6.1 through 10.6.14 and 10.12.1 through 10.12.8, (1991). The multiple sclerosis-associated antigen(s) is a protein that can be isolated from white blood cells. The protein has a molecular weight of between approximately 14,000 to 16,000 daltons as measured on SDS polyacrylamide gels. The protein has been shown to be present in patients suffering from multiple sclerosis.

The present invention also includes a method for preparing monoclonal antibodies produced by cloned B hybridoma cell line(s) against a multiple sclerosis-associated antigen(s). Hybridoma formation and monoclonal antibody production may be effected by many different techniques which are well-known in the art. Standard techniques for immunization, testing, fusion, culturing and cloning are used, as described in Zimmerman, et al. "*Commercial Applications of Monoclonal Antibodies to Bacteria*" (1985), Vol. II pp. 283–320, which is incorporated herein by reference. As stated in that work, the objective is to have specific antibodies that could be purified and used successfully in a variety of procedures, including immunoassays.

According to the present invention, these antibodies are made by hybrid cell lines derived from the fusion and cloning of antibody-producing cells using, for example, immune spleen lymphocytes and a fusion partner, such as the cell line SP2/0. The immune spleen lymphocytes are prepared from a single cell suspension made from the spleens of BALB/c mice known to be producing antibodies to the antigen(s). This reactivity is verified by Western blot and enzyme-linked immunosorbent assay ("ELISA") techniques on sera samples from immunized mice. These antibodies can react against epitope(s) on the surface of the antigen(s) and are derived from a cloned cell line(s).

The antibodies which are produced as described herein are specific for the multiple sclerosis-associated antigen(s) and are characterized according to isotype: HB11152 produces 6D4, which is an IgG subclass 3; and HB11153 produces 3D3, which is an IgM antibody. As the hybridomas grow indefinitely, they provide a continuous source of a single antibody. The two hybridomas were deposited on Oct. 9, 1992, American Type Culture Collection ("ATCC") patent repository collection located at 12301 Parklawn Drive, Rockville, Md. 20852, and are designated as HB11152 and HB11153.

In addition to using purified monoclonal antibodies for coating as a capture reagent, other areas where the assay can be enhanced for specificity, sensitivity and assay conditions include, but are not limited to, the use of: 1) direct enzyme (including, but not limited to, horseradish peroxidase, alkaline phosphatase, glucose oxidase, and urease) conjugated antibodies or anti-biotin antibodies, 2) biotin-conjugated monoclonal antibodies 3) bio- or chemiluminescent labeled antibodies, 4) fluorescent labeled antibodies and 5) radiolabeled antibodies.

The antibodies specific for the multiple sclerosis-associated antigens can be used in a number of different diagnostic tests. Such assays include, but are not limited to, ELISA, Western blot, radioimmunoassay, bioluminescent assay, and chemiluminescent assay. Such immunoassays are well-known in the art; protocols are found, for example, in Chapter 2 of *Current Protocols in Immunology*, Coligan, et al., editor, Green Publishing Associates & Wiley Interscience, 1991.

The procedure and results of a sandwich ELISA using the antibodies according to the present invention is described in Example 11 and 12.

One example of an assay utilizing the antibodies specific for the multiple-sclerosis antigens according to the present invention is the ELISA procedure. In accordance with the present invention, a blood sample is drawn from a human. Preferably, the peripheral blood lymphocytes ("PBL") are isolated from the blood sample, and then processed to extract the multiple sclerosis-associated mitogens from the whole PBLs if they are present. The present invention includes the use of the nucleotide sequences or fragments thereof associated with the protein moiety of multiple sclerosis for the diagnosis of multiple sclerosis or multiple sclerosis related diseases using procedures such as northern or Southern hybridization techniques or nucleotide sequences.

Next, the PBL extract is introduced into a well-shaped container which contains multiple sclerosis-antigen specific antibodies which are already bound to the container. The "capture" antibodies are reactive for the multiple sclerosis-associated antigens. The multiple sclerosis-associated antigens present in the PBL extract will then bind to the antibodies which are bound to the container.

Next, a second set of antibodies, the "primary" antibodies, that are specific for the multiple sclerosis-associated antigens are added to the mixture. These primary antibodies will bind only to the multiple sclerosis-associated antigens that are already bound to the capture antibodies bound to the container. The primary antibodies also differ in that they were modified by the addition of a label, such as an enzyme. The conatiners are then rinsed to remove all unbound antibodies. The label will therefore only be present to the degree that the multiple sclerosis-associated antigens are present.

In the alternative to the above-described assay, the assay may be performed using three different antibodies. Instead of the primary antibody being conjugated, a secondary, conjugated antibody could be used which is selective for the primary antibody. The use of a secondary conjugated antibody amplifies the resultant signal. Alternatively, biotin-labeled antibodies with either avidin or streptavidin labeled enzymes or anti-biotin antibodies conjugated to enzymes could be used.

Whether or not a primary, conjugated antibody or a two-step primary plus secondary, conjugated antibody is used, the conjugated antibody may be labeled with a member selected from the following group: a radioactive isotope, an enzyme, a fluorogenic material, or a luminescent marker. The determination of whether multiple sclerosis-associated antigens are present may be conducted by the following corresponding means: radiometric means, enzymatic means, fluorometric means, and luminescent means.

For all such diagnostic uses, the antibodies and other necessary reagents and appropriate devices may be provided in a kit for convenient, accessible assays.

The present invention also provides a method and composition for alleviating the symptoms of multiple sclerosis and multiple sclerosis-like diseases. The present invention comprises administration to the human or animal with a demyelinating disease such as multiple sclerosis an effective dose of multiple sclerosis-associated antigens or a fraction thereof as or its associated nucleotide sequences or a fraction thereof. The effective dose is at a level which does not cause an anaphylactic response.

In the present invention, multiple sclerosis associated factors means one or several of multiple sclerosis associated proteins, fractions or derivatives of the multiple sclerosis associated proteins or RNA or DNA nucleotide sequences, or fractions thereof, that are associated with the multiple sclerosis associated protein moiety. In practice, the present invention comprises the administration of less than approximately $10^{-2}$ mg per dosage unit to a human or animal with multiple sclerosis. A preferred dose of multiple sclerosis-associated factors or its associated nucleotide sequences or a fraction thereof, or active derivative thereof, is between approximately $10^{-2}$ mg to $10^{-10}$ mg. A more preferred dose of multiple sclerosis-associated factors is between approximately $10^{-4}$ mg and $10^{-8}$ mg. The most preferred dose of multiple sclerosis-associated factors is approximately $10^{-7}$ mg. Preferably, the total periodic daily dosage does not exceed about $10^{-2}$ mg per subject, and still more preferably does not exceed from about $5\times10^{-3}$ to $10^{-4}$ mg.

The present invention comprises the administration of an amount not to exceed approximately $10^{-2}$ mg, although, in certain cases, the total amount of multiple sclerosis-associated factors administered in any one day may exceed the preferred limit. The multiple sclerosis-associated factors can be administered as a liquid or they can be administered as a solid wherein the multiple sclerosis-associated factors are embedded or admixed in a biodegradable or bioerodible matrix. The matrix can be a time release matrix. These matrices are well known to those of ordinary skill in the art and are not critical to the present invention. The multiple sclerosis-associated factors can be administered by preferably subcutaneous injection or by sublingual route. Other routes of injection can be used such as intramuscular, parenteral, intravenous or transdermal.

In one embodiment, the delivery vehicle is an aqueous solution that is contained within an inert container. In another variation, the composition is in the form of a suppository. The liquid form of the composition is preferably injected subcutaneously, although other routes of injection are contemplated as part of the present invention. In addition, the composition can be administered through the mucosal membranes such as nasal membranes. The liquid carrier includes, but is not limited to, 0.1% phenol in saline (0.9% NaCl). Other pharmaceutically acceptable carriers can be used to administer the multiple sclerosis-associated factors.

The multiple sclerosis-associated factors can be administered through standard methods, including, but not limited to, intramuscular and subcutaneous routes. The multiple sclerosis-associated factors can also be administered by sublingual and intranasal routes. Because the effective amount of multiple sclerosis-associated factors in a dose is so low, the composition according to the present invention can also be administered transdermally, anally or orally. The dosage units can be either liquid or solid. Typically, the dosage unit may be administered up to a maximum of about 4 times per day although a larger number of doses may be administered in certain cases.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Collection, Isolation, and Homogenization of Antigenic PBLs is Performed as Follows:

Blood samples from patients diagnosed as having multiple sclerosis, or other neurological conditions, were provided by Dr. Gary Duncan of Neurology Associates, Nashville, Tenn. In addition, members of a multiple sclerosis support group in Greenville, S.C. also provided blood samples.

The antigenic peripheral blood lymphocytes ("PBL") are prepared from persons suffering from multiple sclerosis or other conditions as follows: Blood is collected by venipuncture from an arm vein, unless otherwise indicated. Approximately 17 ml is collected from each individual into two yellow cap Vacutainer Brand Evacuated Blood Collection Tubes (Becton-Dickinson, Baltimore, Md.). Each tube has an 8.5 ml draw and each contains 1.5 ml of Acid Citrate Dextrose Solution, which acts as an anticoagulant. The filled sealed tubes, kept at room temperature (15°–30° C.), are shipped by overnight carrier from the various collection sites to the laboratory of Cell Med, Inc. in Columbia, Md.

Upon receipt, the samples are resuspended by inverting the tubes several times just prior to centrifugation. The tubes are centrifuged for 10 minutes at 2000 RPM using an IC centrifuge. The buffy coat at the plasma/cell interface is collected using disposable plastic Pasteur pipettes and the volume is taken to a total of 6.5 ml using phosphate buffered saline ("PBS"). The PBS consists of 9.0 g/l NaCl, 0.8 g/l $Na_2HPO_4$, and 0.15 g/l $KH_2PO_4$ with the pH adjusted to 7.4. Equal amounts of the buffy coat material are layered over 3 ml of a commercial separation media (Histopaque H-1077 from Sigma Chemical Company, St. Louis, Mo.) in two 15 ml centrifuge tubes. The material is then centrifuged for 40 minutes at 2000 RPM. PBL can also be separated from whole blood layered on top of the Ficoll.

After the centrifugation step, the PBL-enriched interface is collected with a Pasteur pipette and brought up to a total of 15 ml with PBS, pelleted by centrifugation for 10 minutes and resuspended in 3 ml of PBS. The material is forced back and forth through a 5 ml pipette at least 5 times and transferred to a Dounce Glass Homogenizer. The cells are homogenized by 20 up and down passages of the pestle. Alternatively, the cells are disrupted and then homogenized by passage through a 27 gauge needle 20 times. These extracted materials are then stored frozen at −70° C.

When too many samples are received for rapid processing, the PBLs may be collected in PBS after the Histopaque step, and instead of resuspension in PBS for homogenization, the cells may be resuspended in 1 ml of Cryomedia (RMPI 1640, 10% fetal bovine serum, and 7.5% dimethylsulfoxide) and frozen at −70° C. Then the cells are thawed at 37° C., diluted with 13 ml of PBS, collected by centrifugation for 10 minutes at 2000 RPM, resuspended in PBS and homogenized as above.

EXAMPLE 2

Preparation of PBL Extracts for the Immunization of Rabbits and Mice is as Follows:

PBL extracts prepared from multiple sclerosis patients are pooled to have sufficient materials of a representative number of multiple sclerosis patients to immunize several animals. When an immunogen pool is made, all the material is thawed, mixed by inversion several times, pooled in a clean container and then mixed before being aliquoted into 2 ml cryovials in 2 ml quantities. The protein contents, determined by the Pierce BCA Method (Pierce Rockford, Ill.), are between 0.8–1.1 mg/ml for several representative different lots. This material is then stored frozen at approximately −70° C. until ready for use.

For immunization purposes, the antigen(s) described above is thawed and mixed with an equal quantity of Freund's adjuvant (Sigma Chemical Company, St. Louis, Mo). The adjuvant is either complete, for the initial inoculation, or incomplete, for follow-up immunizations.

The mixture is emulsified by vortexing it in a tightly capped vial containing glass beads (4–6 mm diameter). The emulsified preparation is allowed to sit, undisturbed, for 10 minutes to ensure that the emulsion is stable and not separating prior to transfer into a syringe and administration to the animals.

EXAMPLE 3
Immunization of Rabbits and Mice to Generate Antisera to the Multiple Sclerosis-Associated Factors.

Each rabbit (New Zealand White, 4–6 pounds each) is inoculated in at least two sites, one on each side. Each inoculation consists of 0.5 ml of the emulsified preparation described above. For the mice (Balb/C, Harlan Sprague Dawley, Indianapolis, Ind.), the total immunization dosage is 0.1 ml, intraperitoneally. Normally, the rabbits are immunized and test bled at 0, 14, 28 and 42 days. Rabbit blood is collected from the ear vein by venipuncture, allowed to clot, and then the sera is separated from the cellular elements on the same or next day. Mice are test bled only once or twice by orbital or tail vein collection. If other procedures are to be performed, such as inoculation with antigen, then all test bleedings are taken before the immunization procedure is done.

EXAMPLE 4
An Analysis of the Immune Response is Made as Follows:

The sera from the immunized mice and rabbits are then tested for specific reactivity to multiple sclerosis associated antigen(s) by a variety of procedures, most notably ELISA and WB techniques.

First, microassay plates (High binding, Nunc, Helsinki, Finland) are coated by physical absorption of the immunizing antigen(s) at the optimal dilution, previously determined to be between approximately 1/100 to approximately 1/1000, in bicarbonate buffer (1.602 g/l $Na_2CO_3$, 2.93 g/l $NaHCO_3$, and 0.2 g/l $NaN_3$) for one to seven days at approximately 4° C. Prior to use, the coated microassay wells are blocked with 0.2% Bovine Serum Albumin ("BSA") in PBS (0.2% BSA/PBS). Other blocking agents, such as gelatin and hydrolyzed skim milk, can be used. After blocking for 15 minutes, the plates are washed with PBS with 0.05% Tween 20 (both the BSA and Tween are from Sigma Chemical Company). All incubations are at approximately 37° C. for 1–2 hours.

Sample, conjugate and substrate volumes used are 100 µl/well with five 200 µl volume washings using the wash buffer PBS-Tween. Sera samples containing antibody(s) are diluted approximately 1/100, or greater, in PBS. The conjugates (HRP-anti-mouse or HRP-anti-rabbit purchased from Kirkegaard and Perry Laboratories ("KPL"), Gaithersburg, Md.) are diluted 1/1000 in 5% BSA in PBS. The color is derived by conversion of the substrate, o-phenylenediamine ("OPD") (Sigma Chemical Company) to a yellow product and conversion at the termination of the reaction by addition of 100 µl per well of 4N sulfuric acid which results in an orange product. The orange product is read at 490 nanometers on a Bio Tech ELISA plate reader.

In summary, the sequence of reactions in the procedure is: coat, block, wash, antibody solution, wash, conjugate solution, wash, substrate, stop solution and reading.

FIG. 1 illustrates the results of the immunoassay on the antisera obtained from several rabbits immunized with the multiple sclerosis PBL extract and tested with multiple sclerosis antigen(s) or a extract from normal cells. Samples were collected on the days shown on the X axis. The arrows indicate the points when the animals were given immunizations. FIG. 1 shows that certain antigens were present in the multiple sclerosis extract that were not found in the normal extract.

Figure 3:
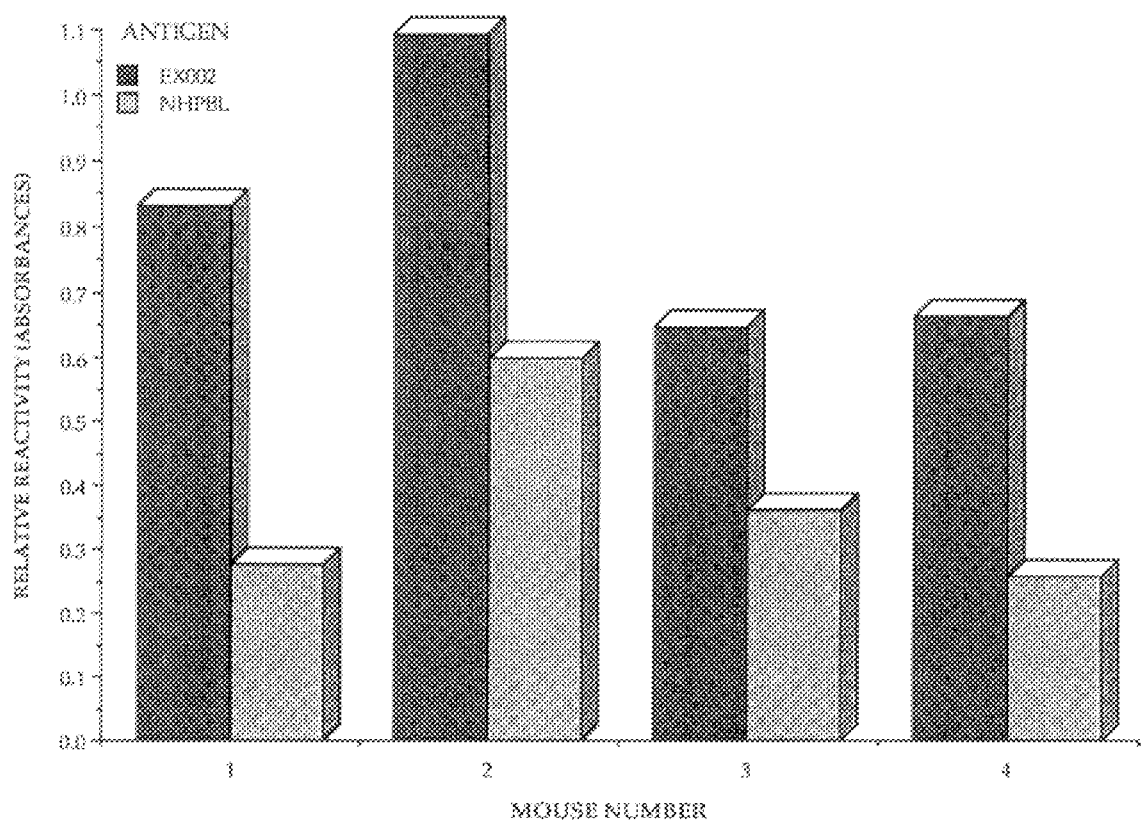
FIG. 3 shows the results of an analysis of the sera from mice immunized with multiple sclerosis associated antigens.

EXAMPLE 5
Response in Murine System:

FIG. 3 shows the results of an analysis, as described in Example 4, for murine immune response, but with only a single time point as multiple collections are not practical. As with the rabbits, it is evident that certain antigens were present in the multiple sclerosis extract that were not found in the normal extract. Western Blot analysis confirmed this fact. Also, certain antigens recognized by the mice and rabbits exhibited the same mobility.

EXAMPLE 6
Western Blot Analysis of Antisera Against the Immunizing Antigen(s):

Extracts of PBL from multiple sclerosis or normal patients are processed and electrophoresed as recommended by the manufacturer of the chemicals and equipment (Mini-Gel Apparatus, Bio-Rad Laboratories, Richmond, Calif.). After electrophoresis, the samples are transblotted, as recommended, then blocked with the same 0.2% BSA as described above.

An electrophoretic separation of various proteins is done under conditions using SDS and mercaptoethanol treatment. This process allows the basic subunit polypeptide chains to be separated from one another as a function of their molecular weights. These electrophoresed materials are then transferred from the polyacrylamide gels ("PAGE") to a support, such as nitrocellulose paper, which binds proteins.

Incubations of the transblotted nitrocellulose paper with the rabbit or murine antibodies ("anti-multiple sclerosis") are at room temperature for approximately 2 hours and all washings use the same wash buffer (PBS-Tween) as in Example 4. The samples containing antibodies are diluted 1/100 in PBS. The conjugate, alkaline phosphatase anti-rabbit or anti-murine IgG (from KPL), is diluted in 5% BSA in PBS. The positive color reaction results from conversion of the BCIP/NBT Substrate (from KPL) to an insoluble blue color.

To summarize the sequence of reactions: antibodies, wash, alkaline phosphatase anti-rabbit IgG (or alkaline phosphatase-anti-mouse if murine antibodies are in use) conjugate, wash, BCIP/NBT substrate and lastly, water, to stop the reaction.

Figure 2:
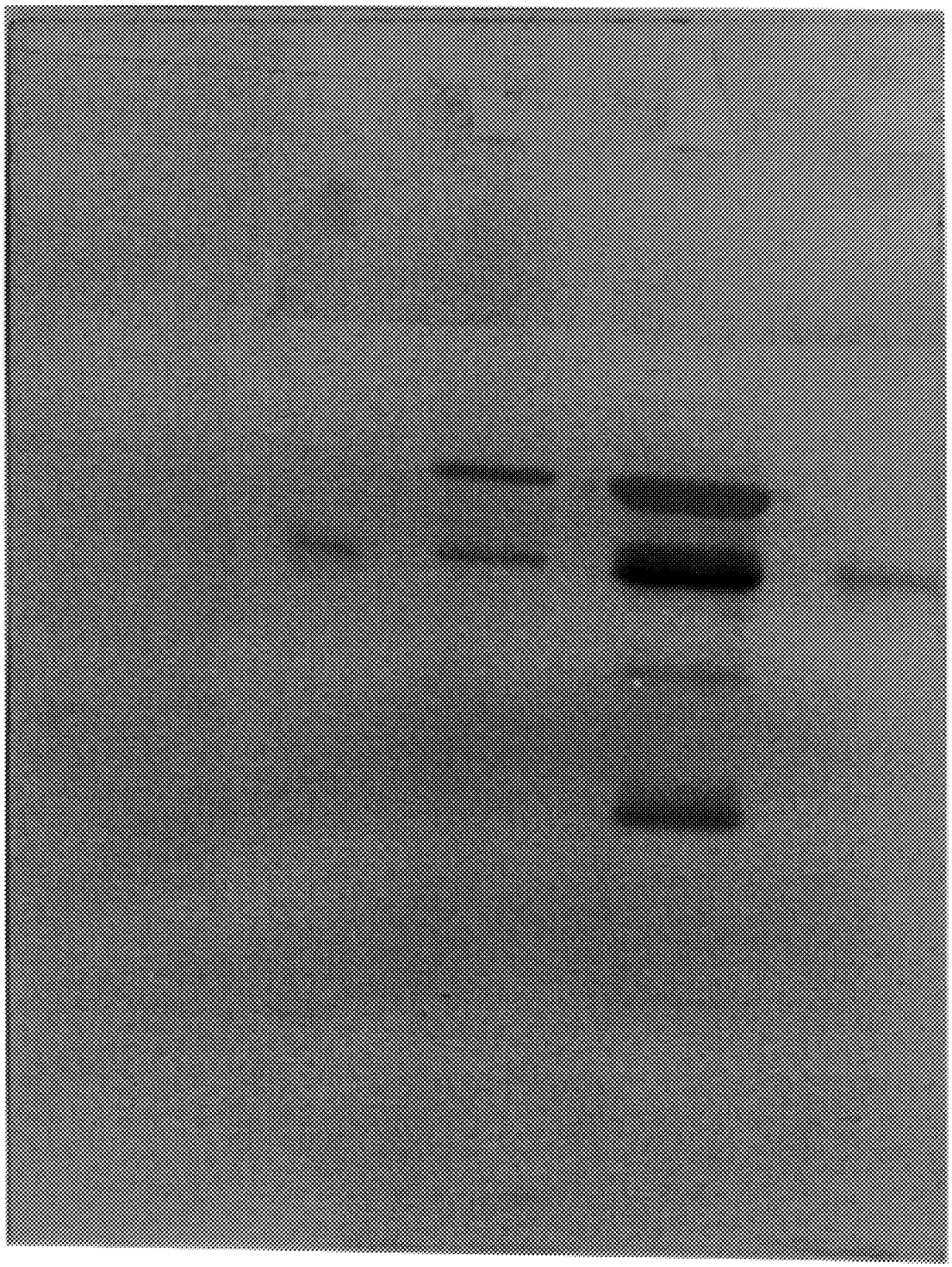
FIG. 2 shows the results of a Western blot analysis of PBL extracts from PBLs from multiple sclerosis patients and normal patients.

A selected serum sample is tested against a sample of normal or multiple sclerosis PBL extracts, according to the recommendations of Bio-Rad. This sample results in a pattern with two major bands and several minor bands on the solid support media which appear to be unique to the multiple sclerosis extract (FIG. 2). The use of molecular weight standards allows a determination of a molecular weight of 14,000 to 16,000 daltons for the smaller band, which is the one easily seen with the monoclonal antibodies. The other larger bands may reflect a precursor form, as is often seen, or an altered form such as a heavily glycosylated one, or a non-reduced form. The murine monoclonal reacts primarily with the lowest molecular weight band.

EXAMPLE 7
Processing and Conjugating of Rabbit Anti-Multiple Sclerosis Antigen IgG.

The antisera from rabbit 5866, taken at day 42, was processed by the standard technique of 40% ammonium sulfate precipitation, followed by dialysis of the redissolved precipitated protein against 0.01M sodium phosphate, pH 7.2, and DEAE chromatography DE-52, following the manufacturer's recommendation (Whatman, Freehold, N.J.). Five ml of the solution containing these antibodies are then absorbed extensively with normal PBL extract coupled to Affi-Gel 10 (Bio-Rad Laboratories). Finally, conjugation of the anti-multiple sclerosis rabbit IgG to Biotin, with NHS-Biotin, is done according to the manufacturer's recommendation (Pierce Chemical, Rockford, Ill.). The biotin rabbit anti-multiple sclerosis conjugate in this case is recognized by Streptavidin-HRP enzyme (KPL).

EXAMPLE 8
Use of Murine Immunoglobulin in an ELISA Test Assay:

The multiple sclerosis antigens may be detected by the use of an ELISA assay wherein a purified monoclonal antibody is used to coat microassay wells and serves to capture the antigen(s) derived from an extract of multiple sclerosis PBL. The immobilized antigen(s) is then detected and a signal is generated by use of a second antibody.

In this example, a polyclonal derived from rabbits was used. The murine antibodies from Mouse 2 are used for an initial study. The murine immunoglobulins are prepared by a 40% ammonium salt cut, similar to that in the rabbit IgG initial step of purification as described in Example 7. The mouse immunoglobulin is used to coat microassay plates in the coating buffer, but at a protein concentration of 5 $\mu$g/ml. The plates are blocked and washed in the same manner as described in Example 4.

This assay is similar to the assay for antibody detection described in Example 4, except the plates are coated with antibodies, blocked, washed, incubated with PBL antigenic extract, washed as before, incubated with antibody conjugate, washed, incubated with a second conjugated species (if needed) and incubated with enzyme substrate. The enzyme is bound only when one or both antibodies, if a double antibody system is used, have detected the antigen (s). The volumes are, however, halved to 50 $\mu$l. Incubations are approximately 1–2 hours long, at approximately 37° C. The antibodies can be directly conjugated to horseradish peroxidase ("HRP") or alkaline peroxidase ("AP").

Finally, the bound enzyme is able to convert a substrate solution into a solution with a new product. This new product absorbs, or in the case of fluorescent products, emits, at a wavelength different from that of the unreacted substrate.

Figure 4:
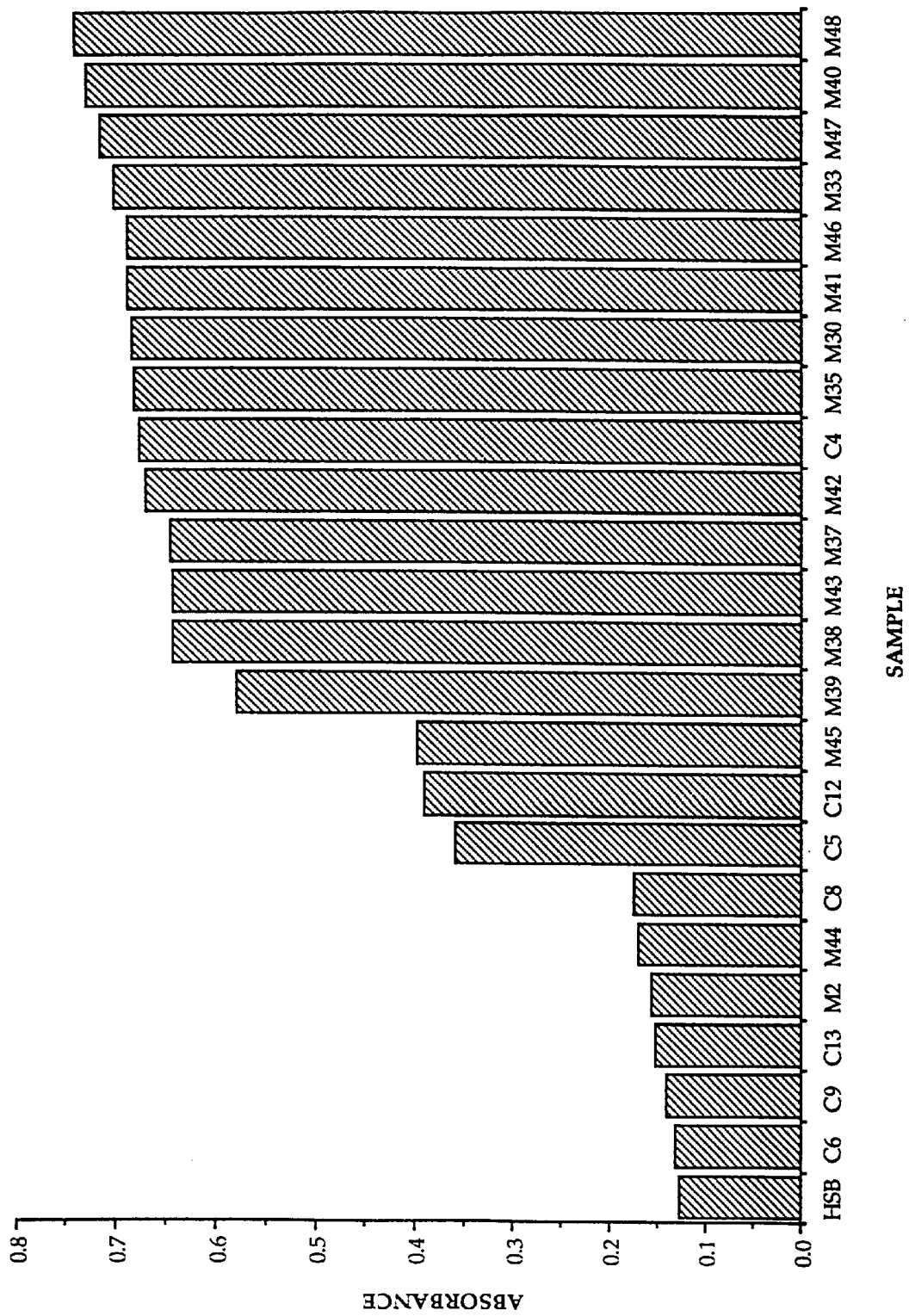
FIG. 4 is a graph showing the results of an ELISA assay of sera from normal patients and patients diagnosed with multiple sclerosis using polyclonal antibodies against multiple sclerosis associated antigens.

FIG. 4 is an analysis of normal patients and patients diagnosed with multiple sclerosis. As shown in the graph, the multiple sclerosis samples are distributed around the higher end of the scale and the known negatives at the lower end.

EXAMPLE 9
Creation of the HB11152 and HB11153 Hybridomas Deposited at the ATCC:

For the generation of monoclonal antibodies, Balb/C mice are immunized, as described in Example 3, with the two pools of multiple sclerosis-PBL antigens: one from South Carolina patients, and an earlier one from a group of Tennessee patients.

For the hybridomas described in this invention, the animals are sacrificed by cervical dislocation and a standard single lymphoid cell preparation is made by disrupting the spleen capsule and freeing lymphocytes from other connective tissue components using a back and forth mechanical process between two frosted glass slides. The spleen cells are washed twice in serum free media and a PEG fusion is done. The cells are incubated in hypothanzine aminopterine thymidine (HAT) media at approximately 37° C., in a 100% relative humidity, 95% air, 5% $CO_2$ atmosphere. The cells are observed on a scheduled basis for growth starting on day 10.

The microwell cultures plated from the fusion are washed and the cells re-fed with HAT media, RPMI 1640 supplemented with Sigma Chemical's "Hybrimax", consisting of 10% Fetal Blood Serum ("FBS"), OPI (oxaloacetic acid, pyruvic acid and insulin), Fungizone, Penicillin and Streptomycin. Starting on day 10, the wells are observed for growth of potential hybridomas, overgrowth of fibroblasts and fungal or bacterial contamination.

EXAMPLE 10
Analysis of Monoclonal Antibodies Produced by the Hybridomas, Created in Example 9:

Table 1 is a summary of results of the characterization of the two monoclonal antibodies raised against an antigenic multiple sclerosis PBL extract. Table 1 gives a summary of these cell lines and their products, the respective monoclonal antibodies. Table 2 compares absorbance signal distribution between these two monoclonal antibodies and a third monoclonal, 2A2.

TABLE 1

Characterization of two monoclonal antibodies raised against an antigenic multiple sclerosis PBL extract.

| Hybridoma or Antibody | Cloning Method | Representative clone(s) | Antibody Isotype | Antigen MW by Western Blot |
|---|---|---|---|---|
| 6D4 | Limiting | 6D4.2 or 3 | IgG3 | 14–16,000 Daltons |
| 3D3 | Limiting | 3D3.2 or 3 | IgM | 14–16,000 Daltons |

TABLE 2

Signal distribution when using crude hybridoma tissue culture fluid as a source of anti-multiple sclerosis capture antibody in conjunction with absorbed biotin labeled rabbit anti-multiple sclerosis antigen

| | Test Antibody | | | | | |
|---|---|---|---|---|---|---|
| | 2A2 | | 3D3 | | 6D4 | |
| Signal Range | N | MS | N | MS | N | MS |
| 0.75–0.85 | 1 | 0 | 1 | 0 | 2 | 0 |
| 0.86–0.95 | 1 | 2 | 1 | 2 | 2 | 0 |
| 0.96–1.05 | 3 | 3 | 2 | 1 | 3 | 2 |
| 1.06–1.15 | 2 | 0 | 3 | 3 | 1 | 3 |
| 1.16–1.25 | 1 | 3 | 1 | 1 | 0 | 1 |
| 1.26–1.35 | 0 | 0 | 0 | 1 | 0 | 0 |
| 1.36–1.45 | 0 | 0 | 0 | 0 | 0 | 2 |

N = Material from 8 normal patients
MS = Material from 8 patients diagnosed with multiple sclerosis The antibody 6D4 is an $IgG_3$ monoclonal antibody that is Western Blot reactive.

Table 2 is an analysis of the distribution of the signals generated with a 1:4 dilution of sera (or plasma) from normal patients and patients diagnosed with multiple sclerosis. The assay uses a coating of affinity purified anti-murine immunoglobulins followed by tissue culture materials with the monoclonal antibodies. Then the assay follows with a patient sample and sequentially biotin-labeled anti-multiple sclerosis rabbit antibody and then Streptoavidin-HRP.

EXAMPLE 11
Preparation of the Coating Antibody for Use in an ELISA Assay is as Follows:

The antibody, 3D3.2, a clone of monoclonal antibody 3D3, is partially purified from ascites materials. First, each ml of ascites fluid is diluted with an equal volume of cold distilled water. Next, an equal amount of 100% saturated ammonium sulfate is added and the sample is thoroughly mixed and left to sit for several hours at approximately 4° C. Afterwards, the precipitated immunoglobulins, including the 3D3.2 IgM, are collected by centrifugation (10,000×G for 15 minutes). The supernatant is discarded and the immunoglobulin precipitate resuspended in a minimal amount of water. The material is then dialyzed against 2× PBS for 3 days, with three buffer solution changes. After dialysis, the sample is clarified and the resultant material stored at approximately −20° C.

For coating purposes, a sample of the frozen antibody is thawed and diluted approximately 1:1000 in the same coating buffer as used in Example 4. The coated microwells are stored at approximately 4° C. in a moist chamber. Before use, the plates are blocked with 0.2% bovine serum albumin and processed as described in Example 4.

EXAMPLE 12

Preparation of the Monoclonal Antibody Conjugate for Use in an ELISA Assay is as Follows.

Another monoclonal antibody (6D4), from clone 6D4.2, is conjugated to horseradish peroxidase, according to the procedure of Nakane, et al., "A Peroxidase Antibody: A New Method of Conjugation" *Histochem Cytochem*, 22:1084, (1974). First, the antibody is purified from ascites material using the Pierce Protein A Antibody Purification Kit as follows: A 1.5 ml sample of ascites is diluted with a 1.5 ml volume of Binding Buffer sample, centrifuged 15 minutes at 10,000×G and applied to a 5 ml staph-A column, washed thoroughly with the binding buffer and then the antibody is eluted with the elution buffer. Since this antibody behaves as a cryoglobulin, especially at or below physiological ionic strengths, all steps are done at room temperature, except the dialysis and centrifugation steps, which are performed at approximately 4° C. Likewise, 2× PBS is used wherever possible, especially since high 6D4 concentrations are preferred. The antibody is conjugated to the enzyme (1:4) following the standard period of activation of the HRP. Separation of unconjugated and conjugated HRP is achieved by ammonium sulfate salt precipitation of the conjugate. The conjugate is dissolved and dialyzed extensively against 2× PBS and stored at approximately −20° C.

The assay is conducted as described in Example 8, except that since the conjugate is HRP-6D4, a single step is needed, not the two steps needed when the Biotin-antibody and Streptoavidin-HRP sequences are used.

Figure 5:
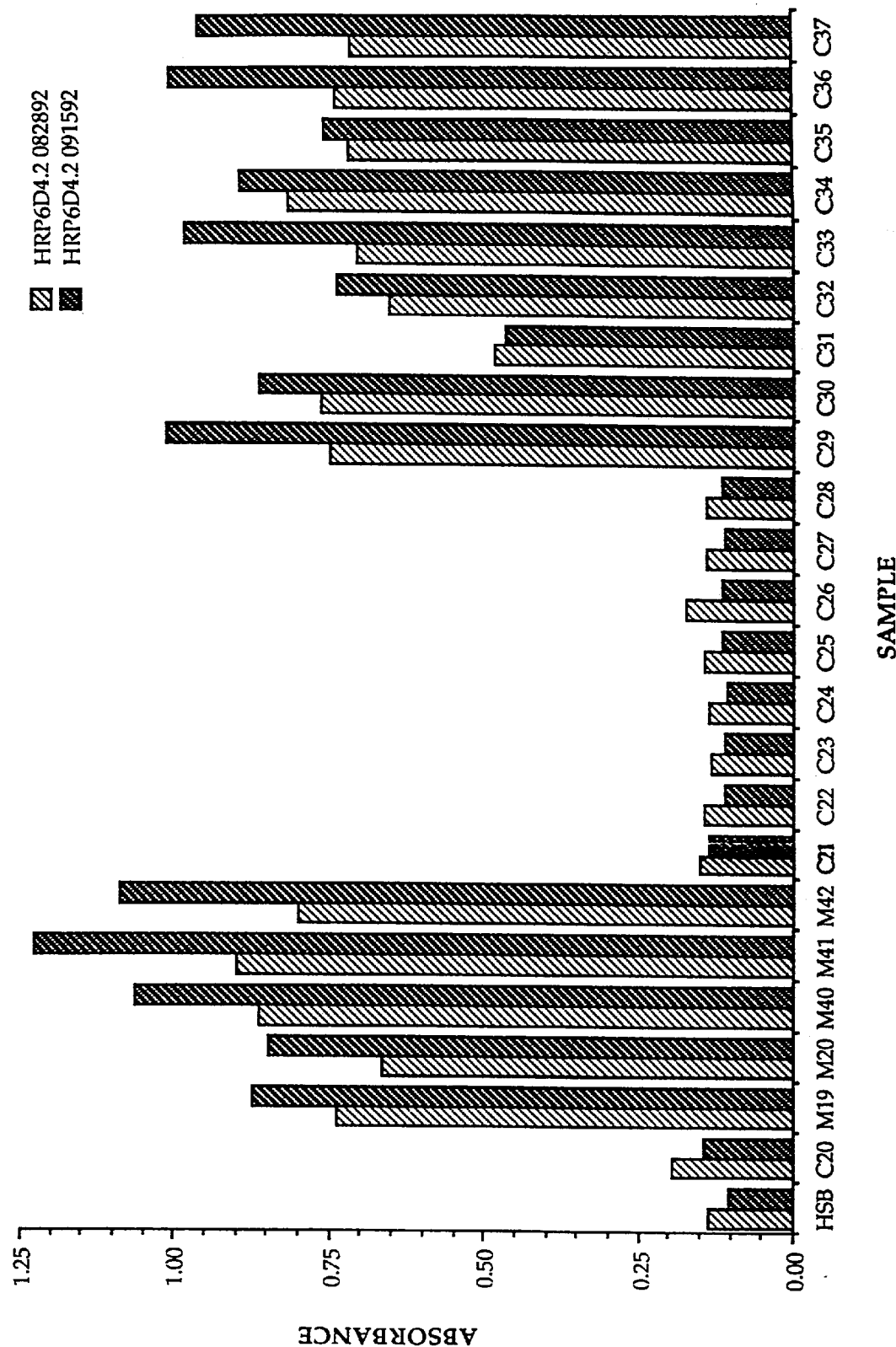
FIG. 5 is a graph showing the results of an ELISA assay of sera from normal patients and patients diagnosed with multiple sclerosis using the 6D4.2 monoclonal antibody against multiple sclerosis associated antigen.

The results are shown in FIG. 5, where the first seven samples used were controls with known diagnosis; the last two groups of samples, CU 21–CU 28 and CU 29–CU 37, were tested blind. The first group of samples, received under code, were labeled as CU 21–28; all of these samples tested negative. The second group of samples, labeled as CU 29–37, all tested positive. Once the code was broken and the patients from whom the blood came were identified, the first group consisted entirely of non-multiple sclerosis patients, although one patient was the son of a diagnosed multiple sclerosis patient and one had epilepsy and perineal nerve palsy. The second group of samples was from patients with multiple sclerosis or conditions thought to be pre-multiple sclerosis.

EXAMPLE 13

Several patients diagnosed with multiple sclerosis were tested according to Example 8 using the HRP-6D4.2 conjugate. In addition, 6 patients who did not have multiple sclerosis were also tested according to the procedure in Example 8. The results of these test are shown in Table III.

TABLE III

| Patients | Negative | Positive |
|---|---|---|
| Normals | 6 | 0 |
| MS patients | 0 | 14 |

As can be seen from Table III, the assay using the method according to the present invention is able to descriminate between normal patients and patients that have been diagnosed with multiple sclerosis.

It should be understood, of course, that the foregoing relates only to preferred embodiments of the present invention and that numerous modifications or alterations may be made therein without departing from the spirit and the scope of the invention as set forth in the appended claims.

What is claimed is:

1. An isolated polypeptide capable of selectively binding to an antibody produced by the hybridoma deposited under ATCC accession number EB11152, wherein the polypeptide has a molecular weight of approximately 14,000 Daltons as measured by reducing polyacrylamide gel electophoresis.

2. The polypeptide of claim 1, wherein the polypeptide is isolated from a blood sample.

3. The polypeptide of claim 1, wherein the polypeptide is isolated from a urine sample.

4. The polypeptide of claim 1, wherein the polypeptide is isolated from a human with multiple sclerosis.

5. An isolated polypeptide capable of selectively binding to an antibody produced by the hybridoma deposited under ATCC accession number HB11153, wherein the polypeptide has a molecular weight of approximately 14,000 Daltons as measured by reducing polyacrylamide gel electrophoresis.

6. The polypeptide of claim 5, wherein the polypeptide is isolated from a blood sample.

7. The polypeptide of claim 5, wherein the polypeptide is isolated from a urine sample.

8. The polypeptide of claim 5, wherein the polypeptide is isolated from a human with multiple sclerosis.

9. A composition comprising a pharmaceutically acceptable carrier and a polypeptide capable of selectively binding to an antibody produced by the hybridoma deposited under ATCC accession number HB11152 or capable of selectively binding to an antibody produced by the hybridoma deposited under ATCC accession number HB11153, wherein the polypeptide has a molecular weight of approximately 14,000 Daltons as measured by reducing polyacrylamide gel electrophoresis.

* * * * *

UNITED STATES PATENT AND TRADEMARK OFFICE
CERTIFICATE OF CORRECTION

PATENT NO. : 5,883,227

DATED : March 16, 1999

INVENTOR(S) : Ellis L. Kline and Daniel H. Zimmerman

It is certified that error appears in the above-identified patent and that said Letters Patent is hereby corrected as shown below:

Claim 1. Please change "EB11152" to --HB11152--.

Signed and Sealed this

Twenty-seventh Day of July, 1999

Attest:

Q. TODD DICKINSON

*Attesting Officer*          *Acting Commissioner of Patents and Trademarks*